United States Patent
Palushi et al.

(10) Patent No.: US 12,376,914 B2
(45) Date of Patent: *Aug. 5, 2025

(54) REGISTRATION PROBE FOR IMAGE GUIDED SURGERY SYSTEM

(71) Applicants: Acclarent, Inc., Irvine, CA (US); Biosense Webster (Israel) Ltd., Yokneam (IL)

(72) Inventors: Jetmir Palushi, Irvine, CA (US); Itzhak Fang, Irvine, CA (US); Noam Racheli, Hadera (IL); Oleg Dulger, Yoqneam Ilit (IL); Itamar Bustan, Zichron Ya'acov (IL)

(73) Assignees: Acclarent, Inc., Irvine, CA (US); Biosense Webster (Israel) Ltd., Yokneam (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/233,432

(22) Filed: Aug. 14, 2023

(65) Prior Publication Data

US 2023/0380908 A1 Nov. 30, 2023

Related U.S. Application Data

(63) Continuation of application No. 16/666,782, filed on Oct. 29, 2019, now Pat. No. 11,744,646.

(Continued)

(51) Int. Cl.
*A61B 5/06* (2006.01)
*A61B 34/00* (2016.01)
*A61B 34/20* (2016.01)

(52) U.S. Cl.
CPC ............ *A61B 34/20* (2016.02); *A61B 5/062* (2013.01); *A61B 34/25* (2016.02); *A61B 2034/2055* (2016.02)

(58) Field of Classification Search
CPC ......... A61B 34/20; A61B 34/25; A61B 5/062; A61B 2034/2055; A61B 2034/2068;
(Continued)

(56) References Cited

U.S. PATENT DOCUMENTS 7,720,521 B2   5/2010 Chang et al.
10,561,370 B2  2/2020 Salazar et al.
(Continued)

FOREIGN PATENT DOCUMENTS

WO   WO 2017/182397 A1   10/2017

*Primary Examiner* — Joseph M Santos Rodriguez
*Assistant Examiner* — Zainab Mohammed Aldarraji
(74) *Attorney, Agent, or Firm* — Barnes & Thornburg LLP

(57) ABSTRACT

Tools used within a surgical area may be equipped with sensors that allow them to be tracked within the magnetic field of an image guided surgery (IGS) system. The IGS system may be configured to detect various movement patterns of the tools, which may be mapped to and associated with corresponding actions or inputs to the IGS system. In one example, a registration probe may be moved along the x-axis and y-axis, with detected movements identified and received by the IGS system as movements of a mouse cursor on a display of the IGS system. In another example, the registration probe may be moved in a circular pattern, or quickly moved along any of the x-axis, y-axis, or z-axis, with each being configured to cause the IGS system to zoom a display, change a view, record video, or other actions.

20 Claims, 11 Drawing Sheets

Related U.S. Application Data

(60) Provisional application No. 62/778,442, filed on Dec. 12, 2018.

(58) Field of Classification Search
CPC ...... A61B 2034/105; A61B 2034/2051; A61B 2034/2072; A61B 2017/00207; A61B 2017/00212; A61B 2017/00221; A61B 17/24; A61B 2217/005; G06F 3/0346; G06F 3/017

See application file for complete search history.

(56) References Cited

U.S. PATENT DOCUMENTS

| | | |
|---|---|---|
| 10,959,677 B2 | 3/2021 | Salazar et al. |
| 11,058,493 B2 | 7/2021 | Rafii-Tari et al. |
| 11,069,082 B1 | 7/2021 | Ebrahimi Afrouzi |
| 2008/0319313 A1 | 12/2008 | Boivin et al. |
| 2010/0191088 A1 | 7/2010 | Anderson et al. |
| 2012/0158011 A1 | 6/2012 | Sandhu et al. |
| 2012/0323364 A1 | 12/2012 | Birkenbach et al. |
| 2014/0364725 A1 | 12/2014 | Makower |
| 2015/0157416 A1 | 6/2015 | Andersson |
| 2016/0008083 A1 | 1/2016 | Kesten et al. |
| 2016/0367321 A1 | 12/2016 | Daon et al. |
| 2017/0049517 A1 | 2/2017 | Felder et al. |
| 2017/0119473 A1 | 5/2017 | Clopp |
| 2017/0340389 A1 | 11/2017 | Otto et al. |
| 2019/0192228 A1 | 6/2019 | Salazar et al. |
| 2020/0188031 A1 | 6/2020 | Palushi et al. |
| 2021/0059766 A1 | 3/2021 | Graetzel et al. |
| 2021/0186615 A1 | 6/2021 | Shmayahu et al. |
| 2021/0236233 A1 | 8/2021 | Fuerst et al. |

REGISTRATION PROBE FOR IMAGE GUIDED SURGERY SYSTEM

PRIORITY

This application is a continuation of U.S. patent application Ser. No. 16/666,782 filed Oct. 29, 2019, published as U.S. Pub. No. 2020/0188031 on Jun. 18, 2020, which claims priority to U.S. Provisional Patent 62/778,442, filed Dec. 12, 2018 and entitled Registration Probe for Image Guided Surgery System, the entireties of which are incorporated by reference herein.

BACKGROUND

Image-guided surgery (IGS) is a technique where a computer is used to obtain a real-time correlation of the location of an instrument that has been inserted into a patient's body to a set of preoperatively obtained images (e.g., a CT or MRI scan, 3-D map, etc.), such that the computer system may superimpose the current location of the instrument on the preoperatively obtained images. An example of an electromagnetic IGS navigation systems that may be used in IGS procedures is the CARTO® 3 System by Biosense-Webster, Inc., of Irvine, California. In some IGS procedures, a digital tomographic scan (e.g., CT or MM, 3-D map, etc.) of the operative field is obtained prior to surgery. A specially programmed computer is then used to convert the digital tomographic scan data into a digital map. During surgery, special instruments having sensors (e.g., electromagnetic coils that emit electromagnetic fields and/or are responsive to externally generated electromagnetic fields) are used to perform the procedure while the sensors send data to the computer indicating the current position of each surgical instrument. The computer correlates the data it receives from the sensors with the digital map that was created from the preoperative tomographic scan. The tomographic scan images are displayed on a video monitor along with an indicator (e.g., crosshairs or an illuminated dot, etc.) showing the real-time position of each surgical instrument relative to the anatomical structures shown in the scan images. The surgeon is thus able to know the precise position of each sensor-equipped instrument by viewing the video monitor even if the surgeon is unable to directly visualize the instrument itself at its current location within the body.

IGS navigation systems may be interacted with using various conventional means, such as a keyboard, mouse, or touch screen interface. Such conventional means of interacting with an IGS navigation system may be sufficient during pre-procedure steps. For example, a surgeon may use a keyboard and mouse to navigate through the digital map and tomographic scan data to review instrument paths, anatomical structures, and other information relating to the surgical site. However, such conventional means may be less useful when interacting with the IGS navigation system during a procedure, as a surgeon may have to leave the sterile room to interact with a keyboard and mouse, may have to relay voice commands for adjusting the IGS navigation view to personnel at the keyboard and mouse, or may have to step away from or shift their focus from the patient to interact with a touchscreen within the sterile room. Each such interaction may require various additional steps in order to maintain sterility (e.g., re-sterilizing before returning to the sterile room, changing gloves after interacting with a touchscreen). Additionally, devices intended to be used within the sterile room may need to be specially prepared or specially manufactured so that they can resist contamination, allow for sterilization in between procedures, or be disposed after each procedure, any of which can impact the cost quality, and usability of such devices.

While several systems and methods have been made and used in surgical procedures, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1:
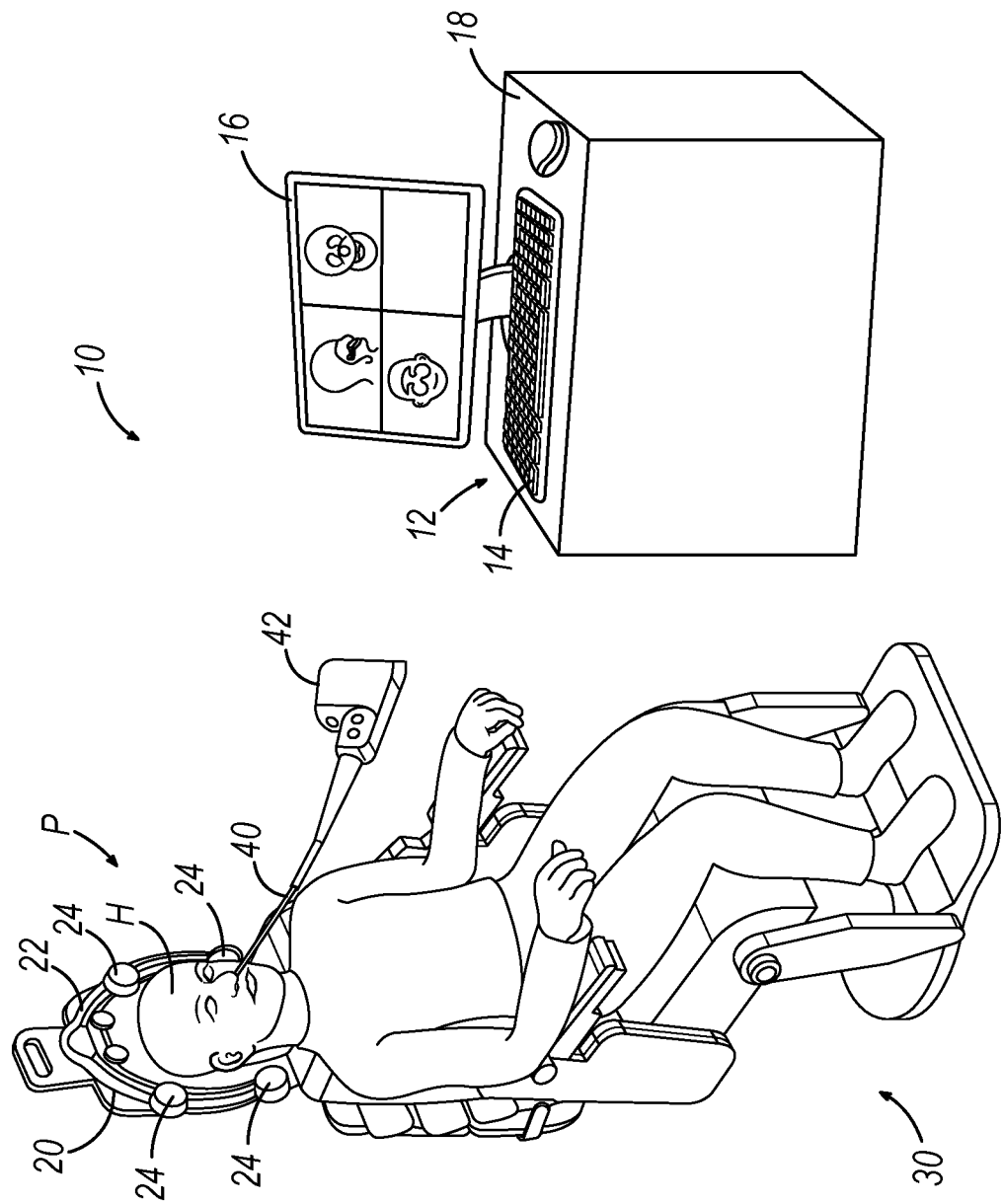
FIG. 1 depicts a schematic view of an exemplary surgery navigation system being used on a patient seated in an exemplary medical procedure chair.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

I. Exemplary Image Guided Surgery Navigation System

When performing a medical procedure within a head (H) of a patient (P), it may be desirable to have information regarding the position of an instrument within the head (H) of the patient (P), particularly when the instrument is in a location where it is difficult or impossible to obtain an endoscopic view of a working element of the instrument within the head (H) of the patient (P). FIG. 1 shows an exemplary IGS navigation system (10) enabling an ENT procedure to be performed using image guidance. In addition to or in lieu of having the components and operability described herein IGS navigation system (10) may be constructed and operable in accordance with at least some of the teachings of U.S. Pat. No. 7,720,521, entitled "Methods and Devices for Performing Procedures within the Ear, Nose, Throat and Paranasal Sinuses," issued May 18, 2010, the disclosure of which is incorporated by reference herein; and U.S. Pat. Pub. No. 2014/0364725, now abandoned, entitled "Systems and Methods for Performing Image Guided Procedures within the Ear, Nose, Throat and Paranasal Sinuses," published Dec. 11, 2014, the disclosure of which is incorporated by reference herein.

IGS navigation system (10) of the present example comprises a field generator assembly (20), which comprises set of magnetic field generators (24) that are integrated into a horseshoe-shaped frame (22). Field generators (24) are operable to generate alternating magnetic fields of different frequencies around the head (H) of the patient (P). A navigation guidewire (40) is inserted into the head (H) of the patient (P) in this example. Navigation guidewire (40) may be a standalone device or may be positioned on an end effector or other location of a medical instrument such as a surgical cutting instrument or dilation instrument. In the present example, frame (22) is mounted to a chair (30), with the patient (P) being seated in the chair (30) such that frame (22) is located adjacent to the head (H) of the patient (P). By way of example only, chair (30) and/or field generator assembly (20) may be configured and operable in accordance with at least some of the teachings of U.S. patent application Ser. No. 15/933,737, entitled "Apparatus to Secure Field Generating Device to Chair," filed Mar. 23, 2018, issued as U.S. Pat. No. 10,561,370 on Feb. 18, 2020, the disclosure of which is incorporated by reference herein.

IGS navigation system (10) of the present example further comprises a processor (12), which controls field generators (24) and other elements of IGS navigation system (10). For instance, processor (12) is operable to drive field generators (24) to generate alternating electromagnetic fields; and process signals from navigation guidewire (40) to determine the location of a sensor in navigation guidewire (40) within the head (H) of the patient (P). Processor (12) comprises a processing unit (e.g., a set of electronic circuits arranged to evaluate and execute software instructions using combinational logic circuitry or other similar circuitry) communicating with one or more memories. Processor (12) of the present example is mounted in a console (18), which comprises operating controls (14) that include a keypad and/or a pointing device such as a mouse or trackball. A physician uses operating controls (14) to interact with processor (12) while performing the surgical procedure.

Navigation guidewire (40) includes a sensor (not shown) that is responsive to positioning within the alternating magnetic fields generated by field generators (24). A coupling unit (42) is secured to the proximal end of navigation guidewire (40) and is configured to provide communication of data and other signals between console (18) and navigation guidewire (40). Coupling unit (42) may provide wired or wireless communication of data and other signals.

In the present example, the sensor of navigation guidewire (40) comprises at least one coil at the distal end of navigation guidewire (40). When such a coil is positioned within an alternating electromagnetic field generated by field generators (24), the alternating magnetic field may generate electrical current in the coil, and this electrical current may be communicated along the electrical conduit(s) in navigation guidewire (40) and further to processor (12) via coupling unit (42). This phenomenon may enable IGS navigation system (10) to determine the location of the distal end of navigation guidewire (40) or other medical instrument (e.g., dilation instrument, surgical cutting instrument, etc.) within a three-dimensional space (i.e., within the head (H) of the patient (P), etc.). To accomplish this, processor (12) executes an algorithm to calculate location coordinates of the distal end of navigation guidewire (40) from the position related signals of the coil(s) in navigation guidewire (40). While the position sensor is located in guidewire (40) in this example, such a position sensor may be integrated into various other kinds of instruments, including those described in greater detail below.

Processor (12) uses software stored in a memory of processor (12) to calibrate and operate IGS navigation system (10). Such operation includes driving field generators (24), processing data from navigation guidewire (40), processing data from operating controls (14), and driving display screen (16). In some implementations, operation may also include monitoring and enforcement of one or more safety features or functions of IGS navigation system (10). Processor (12) is further operable to provide video in real time via display screen (16), showing the position of the distal end of navigation guidewire (40) in relation to a video camera image of the patient's head (H), a CT scan image of the patient's head (H), and/or a computer generated three-dimensional model of the anatomy within and adjacent to the patient's nasal cavity. Display screen (16) may display such images simultaneously and/or superimposed on each other during the surgical procedure. Such displayed images may also include graphical representations of instruments that are inserted in the patient's head (H), such as navigation guidewire (40), such that the operator may view the virtual rendering of the instrument at its actual location in real time. By way of example only, display screen (16) may provide images in accordance with at least some of the teachings of U.S. Pub. No. 2016/0008083, entitled "Guidewire Navigation for Sinuplasty," published Jan. 14, 2016, issued as U.S. Pat. No. 10,463,242 on Nov. 5, 2019, the disclosure of which is incorporated by reference herein. In the event that the operator is also using an endoscope, the endoscopic image may also be provided on display screen (16).

The images provided through display screen (16) may help guide the operator in maneuvering and otherwise manipulating instruments within the patient's head (H) when such instruments incorporate navigation guidewire (40). It should also be understood that other components of a surgical instrument and other kinds of surgical instruments, as described below, may incorporate a sensor like the sensor of navigation guidewire (40).

II. Exemplary Registration Probe with Pattern Tracking

While IGS navigation systems such as the IGS navigation system (10) provide advantages during surgical procedures, conventional tools, devices, and interfaces used to interact with such systems are in some ways limited. In order to leverage the numerous views, perspectives, and details available to a surgeon from the IGS navigation system (10), the tools and devices used to interact with and navigate with that system may benefit from features and functions focused on ease of use during a surgical procedure. For example, a standard computer mouse may be difficult to use in such an environment because it may be difficult to find a contact surface for the optical or mechanical motion tracking element of such a device, and because a surgeon may be wearing gloves, or may have one or both hands already occupied with another tool or task. Similarly, computer keyboards may be difficult to manipulate when wearing sterile gloves, and may not be reusable, or may require cost increasing non-standard features allowing them to be used or reused within a sterile setting (e.g., covers or designs that eliminate areas where contamination can gather, specialized designs that can accommodate later sterilization procedures). Moreover, interacting with user input devices such as a mouse or keyboard may either require the operator to move back and forth between the patient and the user input device or require reliance on an assistant to interact with the user input device. Each of these scenarios may present inefficiencies or otherwise be undesirable.

Devices having features such as non-contact navigation (e.g., devices that, unlike an optical mouse, do not require a contact surface to function) and motion tracking navigation may provide advantages in ease of use during surgical procedures. Additionally, such functionality may also be advantageously integrated with tools and devices already used in surgical procedures, in order to introduce new functionality without introducing entirely new devices or tools.

Figure 2:
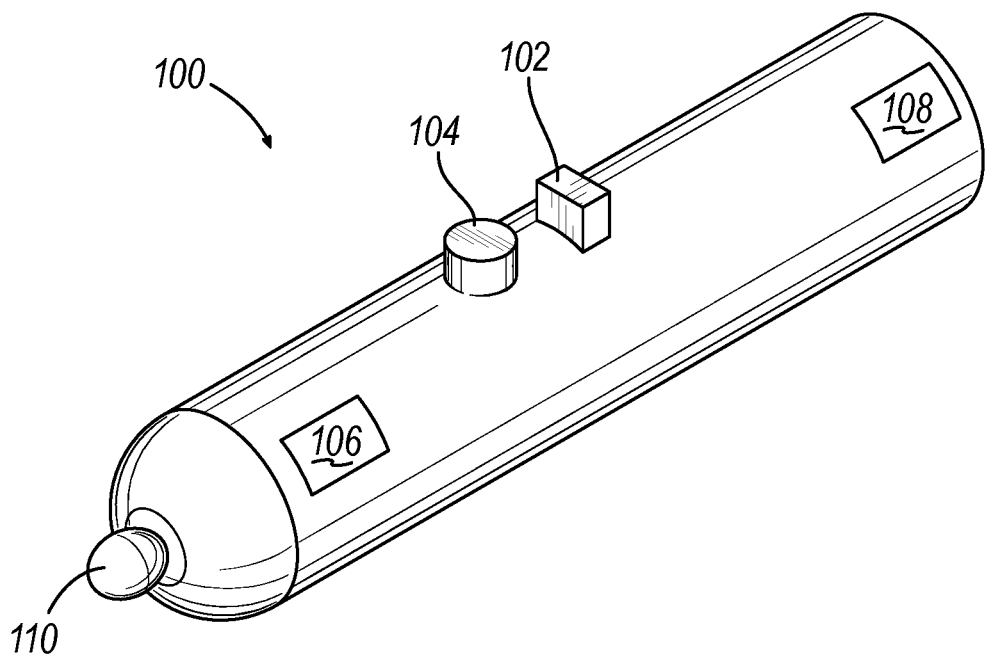
FIG. 2 depicts a perspective view of an exemplary registration probe usable with the surgery navigation system.

For example, FIG. 2 shows a perspective view of an exemplary registration probe (100) usable with a surgery navigation system such as the IGS navigation system (10), that may be implemented having one or more features that aid in interactions with the IGS navigation system (10). A registration probe may be used with some IGS techniques in order to register the location of various anatomical features of the patient (e.g., the location and orientation of anatomical landmarks on the patient's face) to the IGS navigation system (10) so that it can be correlated with the position of one or more tracked instruments. Examples of various forms that registration probe (100) may take, and registration functionalities that may be provided by registration probe (100), are described in U.S. patent application Ser. No. 15/852,169, entitled "Apparatus and Method for Registering Facial Landmarks for Surgical Navigation System," filed Dec. 22, 2017, issued as U.S. Pat. No. 10,786,311 on Sep. 29, 2020, the disclosure of which is incorporated by reference herein; and U.S. Pub. No. 2017/0119473, entitled "System and Method for Navigation of Surgical Instruments," published May 4, 2017, issued as U.S. Pat. No. 10,779,891 on Sep. 22, 2020, the disclosure of which is incorporated by reference herein. The following description provides additional ways in which a registration probe (100) may be used in a manner far beyond the conventional uses contemplated for a registration probe (100) as described in the above-noted references.

Figure 4:
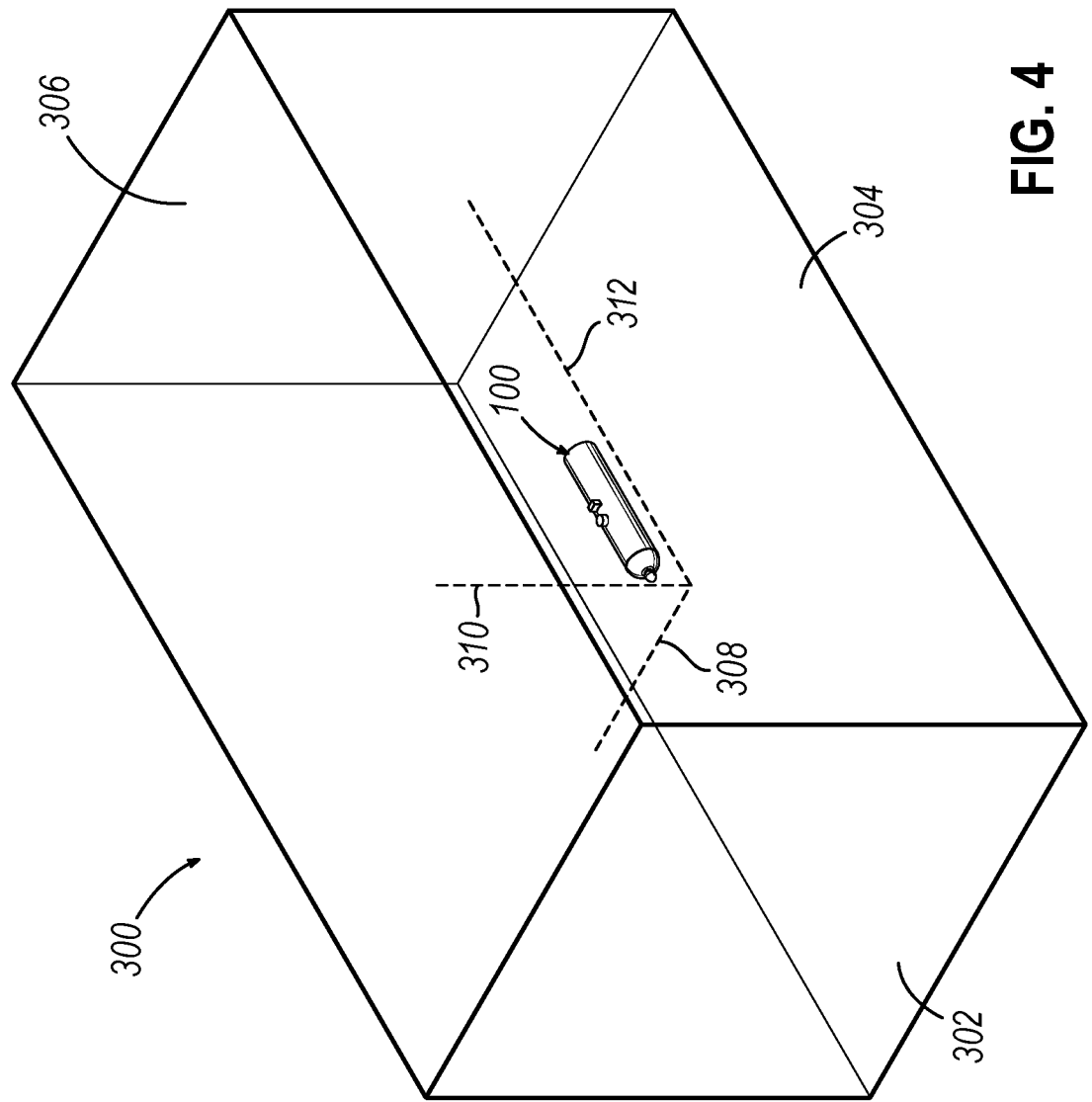
FIG. 4 depicts a diagram showing the registration probe of FIG. 2 being tracked within an exemplary tracked space by the surgery navigation system.

The IGS navigation system (10) provides a tracked space (300) (e.g., an area in which the magnetic field sensors or other sensors can detect the positions and movements of surgical instruments having corresponding sensor elements, as shown in FIG. 4 and discussed in more detail below) in which the position of compatible devices can be tracked. This tracked space (300) is a three-dimensional space of varying sizes and shapes and may include at least the space in which the surgical procedure is performed (e.g., for a surgical procedure in or near paranasal sinuses, in a patient's head); but may also include additional portions of space beyond the particular surgical site (e.g., a space extending several feet in each direction from the patient's head).

While some instruments include elements or features that can be tracked within the tracked space (300), the position of a patient must also be known in order to provide accurate IGS navigation. Since a patient is not inherently trackable by the IGS navigation system (10), the registration probe (100) may be used to locate and register a surgical site, such as the patient's face, with the IGS navigation system (10) so that its position within the tracked space (300) may be determined. By determining the position of the patient's head (H) within the tracked space (300), IGS navigation system (10) may accurately correlate the location of anatomical structures in the patient's head (H) with anatomical structures represented by preoperatively obtained images (e.g., CT scans) and/or digital models, etc. of the patient's head (H) as already stored in IGS navigation system (10).

As shown in FIG. 2, the registration probe (100) includes a position sensor (106) that is compatible with the IGS navigation system (10) and allows the registration probe (100) to be located within the tracked space (300), and also includes additional user inputs such as a first button (102), a second button (104), and a mode switch (108). A patient may be registered by placing a tip (110) of the registration probe against a plurality of points across the patient's face and registering each point (e.g., manually by pressing a button such as the first button (102), or automatically where the tip (110) is configured to detect contact with the patient's face of a sufficient force to cause automatic registration). As each point is registered, the position sensor (106) provides that location, within the tracked space (300), to the IGS navigation system (10), which may use such information to correlate the position of any tracked surgical instruments with the patient's position.

Figure 3:
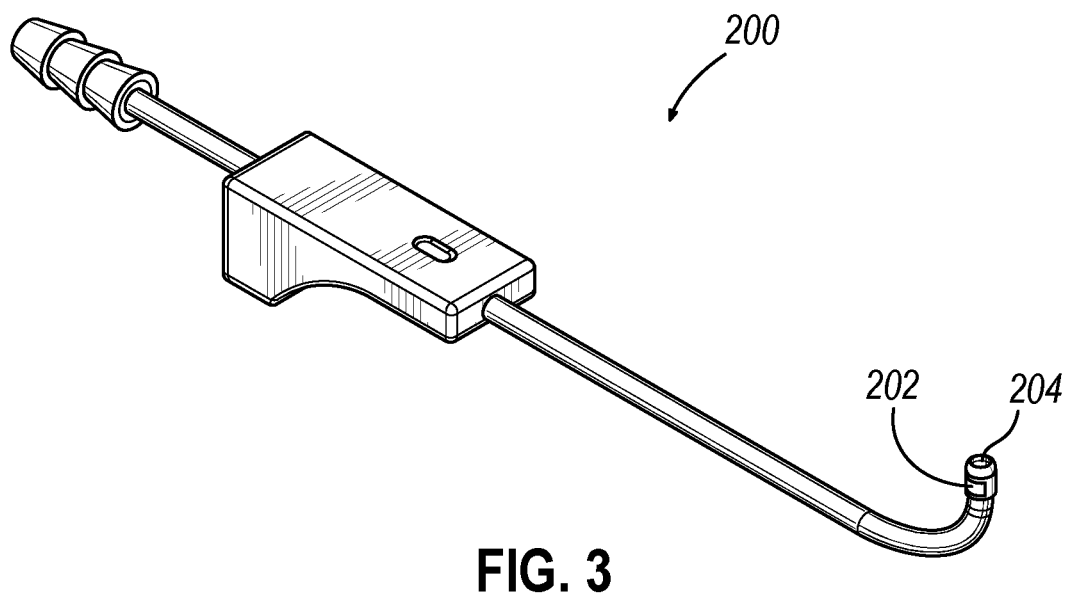
FIG. 3 depicts a perspective view of an exemplary suction instrument usable with the surgery navigation system.

FIG. 3 shows another example of a surgical instrument that may be used with the surgery navigation system (10) to provide one or more features that aid in interactions with the IGS navigation system (10). That figure shows a perspective view of an exemplary suction tool (200) that may be attached to a vacuum source and used to provide suction at a distal tip (204) to remove liquids such as water or bodily fluids from a surgical site. The suction tool (200) includes a position sensor (202) that allows the position of distal tip (204) to be tracked by the IGS navigation system (10) within the tracked space (300), and positionally displayed in real time within the virtual view and preoperatively obtained images of the patient's anatomy to aid in precise placement and use during a surgical procedure.

While each of the registration probe (100) and the suction tool (200) may be used to provide one or more features allowing a surgeon to interact with the IGS navigation system (10), as will be described in more detail below, it should be understood that other surgical instruments that are trackable within the tracked space (300), or that are capable of independently providing signals indicating their position and movements (e.g., by use of accelerometers) and communicating such information to the IGS navigation system (10), may also be advantageously used as described herein. This may include, for example, positionally tracked guidewires, dilation instruments, shavers, endoscopes, cutting tools, and other surgical instruments as will be apparent to those skilled in the art in view of the teachings herein.

FIG. 4 shows a diagram showing a surgical instrument such as the registration probe (100) being tracked within the tracked space (300) by a surgery navigation system such as the IGS navigation system (10). While a tracked space may be of varying sizes and shapes, the tracked space (300) is depicted as being a three dimensional rectangular space in which the registration probe (100) is contained. The registration probe (100) may be tracked in various ways within the tracked space (300) depending upon the capabilities of a particular IGS system and probe (e.g., number and location of position sensors). For example, in some implementations, the registration probe (100) may be tracked with three degrees of freedom (e.g., movement along an x, y, and z axis), while in others it may be tracked with six degrees of freedom (e.g., three degrees of freedom, as well as rotations about the x, y, and z axis). FIG. 4 shows the registration probe being tracked with three-degrees of freedom, represented by dotted lines, which include tracked movement along an x-axis (308), a y-axis (310), and a z-axis (312).

Such movements within the tracked space (300) can be interpreted by the IGS navigation system (10) as movements within the three dimensional space therein, but may also be interpreted as movements within a two dimensional area. When confining movements of the registration probe (100) to two dimensions, it can be seen that the tracked space (300) also includes a first canvas (302), which observes movements of the registration probe (100) along the x-axis (308) and y-axis (310); a second canvas (304), which observes movements along the y-axis (310) and z-axis (312); and a third canvas (306), which observes movements along the x-axis (308) and z-axis (312). Since many IGS navigation system (10) interfaces may be displayed in two-dimensions, interpreting movements of a tracked device such as the registration probe (10) in two dimensions (e.g., the first canvas (302)) may advantageously correspond to such IGS navigation system (10) interfaces. Additionally, movements may also be considered in a single dimension (e.g., only considering movement along the z-axis (312)) to provide further opportunities for input.

Movement based inputs within the tracked space (300), whether three dimensional or less, allow an IGS navigation system (10) to receive a variety of types and magnitudes of input via registration probe (100). For example, without movement based inputs, the registration probe (100) may be limited to input by buttons alone, which may already be assigned to other features (e.g., pressing the first button (102) to register a point on a patient's face), or may not provide a wide variety of input options (e.g., even in combination, three buttons would only provide seven different input types). With movement-based inputs, the IGS navigation system (10) can be configured to detect and act upon various patterns of movement of registration probe (100) rather than only detecting and acting upon activations of buttons (102, 104) of registration probe (100), resulting in a flexible range of inputs.

III. Exemplary Pattern Tracking Methods

Figure 5:
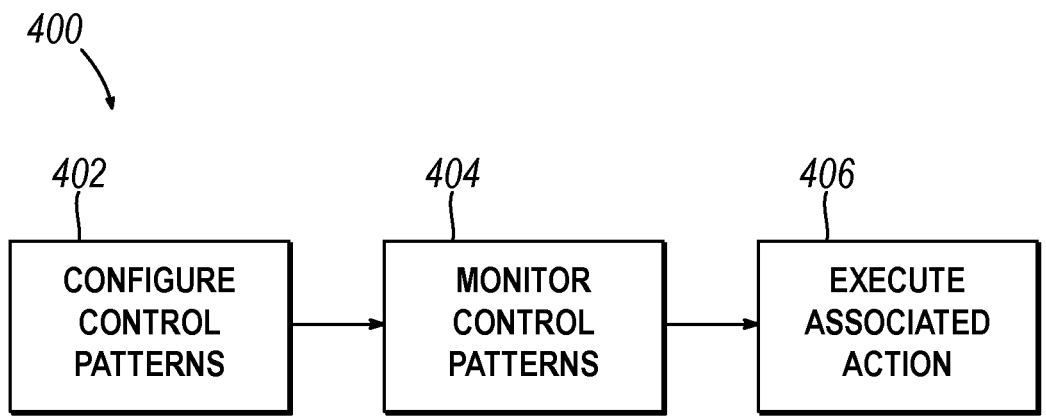
FIG. 5 depicts an exemplary set of high level steps that may be performed to recognize movements patterns within the tracked space.

As an example of providing pattern-based controls for the IGS navigation system (10), FIG. 5 depicts an exemplary set of high level steps (400) that may be performed to recognize movement patterns of registration probe (100) within the tracked space. The IGS navigation system (10) may be configured (block 402) to identify one or more control patterns for movement based inputs, and to react to such patterns in various ways. For example, this could include configuring a control pattern associated with movement of the registration probe (100) relative to the first canvas (302), with the corresponding action being configured to cause a mouse cursor to move on the display screen (16) in a motion mimicking the movement of registration probe (100) relative to the first canvas (302). When receiving movement based inputs from the tracked space (300), the IGS navigation system (10) may monitor (block 404) for configured (block 402) control patterns, and when they are detected, may execute (block 406) one or more associated actions or tasks. Continuing the above example, this could include monitoring (block 404) for movement of the registration probe (100) relative to the first canvas (302) and, when detected, executing (block 406) the associated task to move the cursor on the display screen (16) in a motion corresponding to the movement of the registration probe (100) relative to the first canvas (302).

Figure 6:
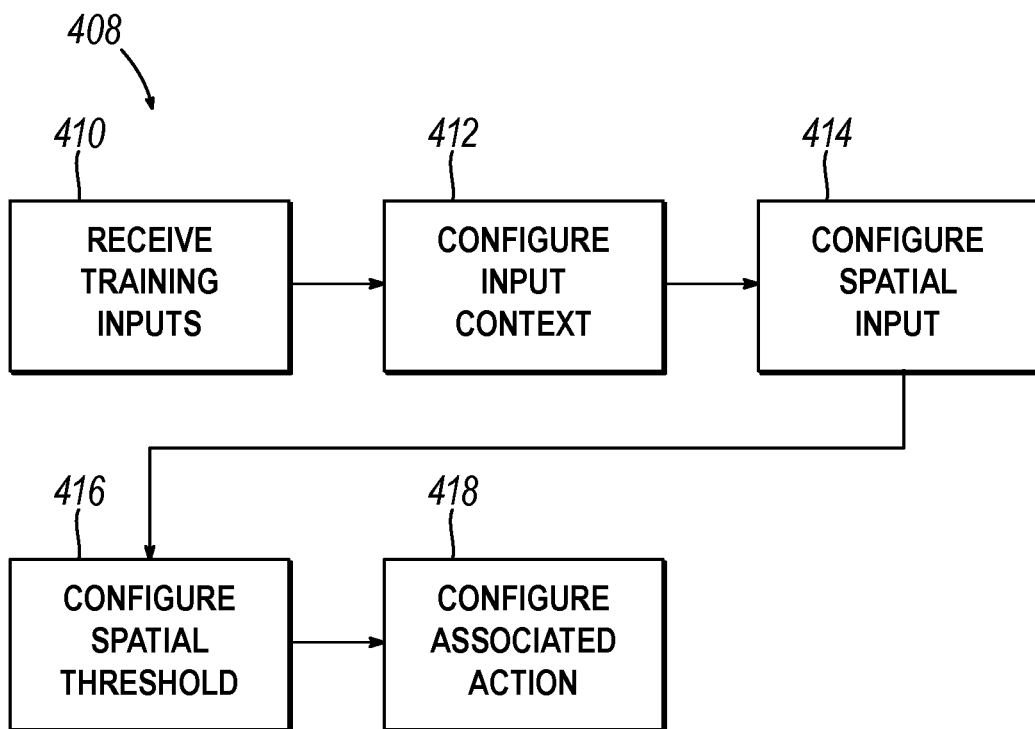
FIG. 6 depicts an exemplary set of steps that may be performed to configure pattern recognition.

FIGS. 6-9 show exemplary sets of more detailed steps that may be performed during one or more of the high level steps of FIG. 5. For example, FIG. 6 depicts an exemplary set of steps (408) that may be performed to configure control pattern recognition for a system such as the IGS navigation system (10). Such configuration may be performed manually by a user, or may be performed automatically in some cases (e.g., by a user interacting with another device as described, or by retrieving other configuration records and preferences associated with a particular user or surgeon). The system may receive (block 410) one or more training inputs that include a pattern of movement of registration probe (100) that is to be monitored. Training inputs may be received (block 410) as selections or inputs of various pre-defined patterns (e.g., a software interface may allow a user to select a predefined pattern of "movement along z-axis"), or may be received as motion input from a device tracked within the tracked space (300) (e.g., a user may move the registration probe (100) within the tracked space (300) in the desired motion, such as along one or more directional axes).

Received (block 410) inputs may include directions of movement over time (e.g., a brief movement in a relatively straight line, or an extended movement in a circular motion), speed of movement (e.g., differentiating a slow movement versus a rapid movement), and other detectable characteristics of movement. Received (block 410) inputs may also be interpreted as movements within three dimensions, two dimensions, or in one dimension, as may be desired.

The system may also configure (block 412) an input context for the control pattern being configured. Input contexts may be chosen from a set of available contexts, dependent upon the IGS navigation system (10) or other tools or devices. As an example, where the IGS navigation system (10) determines that a registration probe (100) is currently being used to register a patient's face, it may be determined that the registration probe (100) is not being used for the purpose of interacting with the display screen (16). When configuring a control pattern for the registration probe (100), the input context may be configured (block 412) to disregard any motion inputs received during registration. Other input contexts may include only recognizing motion input from the registration probe (100) when the first button (102) is depressed, only recognizing motion input from the registration probe (100) when the mode switch (108) is used to place the probe into a motion control mode, or only recognizing motion input from the registration probe (100) at various stages of a surgical procedure being tracked by the IGS navigation system (10) (e.g., differentiating a pre-operative stage of the procedure from a mid-stage of the procedure). In some instances, the IGS navigation system (10) may automatically determine that the procedure has transitioned from a pre-operative stage (e.g., a patient registration stage) to an operative stage (e.g., where actual surgery is being performed) when a surgical instrument such as suction tool (200) is coupled with IGS navigation system (10). In some such instances, the coupling of a surgical instrument such as suction tool (200) with IGS navigation system (10) will trigger a prompt to the user, asking the user to confirm whether the procedure has transitioned from a pre-operative stage to an operative stage.

The system may also configure (block 414) a spatial input based on the received (block 410) inputs. This could include configuring characteristics such as movement along one or more axes, the distance traveled (e.g., differentiating a short linear motion from a longer linear motion, or a small circular motion from a larger circular motion), the speed or acceleration of movements, the frequency of movements (e.g., differentiating singular motions versus repetitive motions), as well as complex movements (e.g., a movement that traces a letter or word). Configuring spatial inputs may include, for example, saving the received (block 410) inputs so that they may be later compared to monitored inputs, converting inputs into a process, rule, or module that receives monitored inputs and returns a match result, or other similar processes.

The system may also configure (block 416) one or more thresholds relating to the configured (block 414) spatial input. The configured (block 416) thresholds allow the user to fine tune the way that that the IGS navigation system (10) interprets their motion inputs for purposes of the control pattern. This could include, for example, setting a high threshold for matching a certain control pattern where the user wants to be deliberate in performing the motion (e.g., a high threshold for a monitored circular motion may only be triggered when the monitored input substantially matches the size and shape of the configured (block 414) circular input), while a low threshold may be more appropriate for complex patterns (e.g., a low threshold for writing a letter in the air may be triggered more easily later, but may result in more false positives). Some configured (block 416) spatial thresholds may also be applied to multiple control patterns, or may be configured (block 416) to apply globally. For example, where a user only wishes to use control patterns that involve movement along the z-axis occasionally, a high threshold may be applied to all inputs received from such movements such that only the largest inputs (e.g., as a magnitude of speed, distance, or acceleration) from the z-axis may be identified as triggering a control pattern.

The system may also configure (block 418) one or more associated actions to be performed when the configured (block 414) spatial input is detected within the correct context and threshold by a monitoring IGS navigation system (10). Associated actions may be selected from a list of available actions, and may include moving a cursor on the display screen (16), switching to a different software application or interface, zooming a displayed interface, capturing a screenshot or video, selecting or clicking on an element of a displayed interface, navigating between images in a set (e.g., stepping through a set of tomographic images one at a time), navigating between pre-defined views (e.g., stepping through pre-defined tomographic images, viewpoints, or perspectives configured prior to a procedure to provide varying viewpoints around a surgical site), and other functionality as will be described below, and as will be apparent to one of ordinary skill in the art in light of this disclosure.

Figure 7:
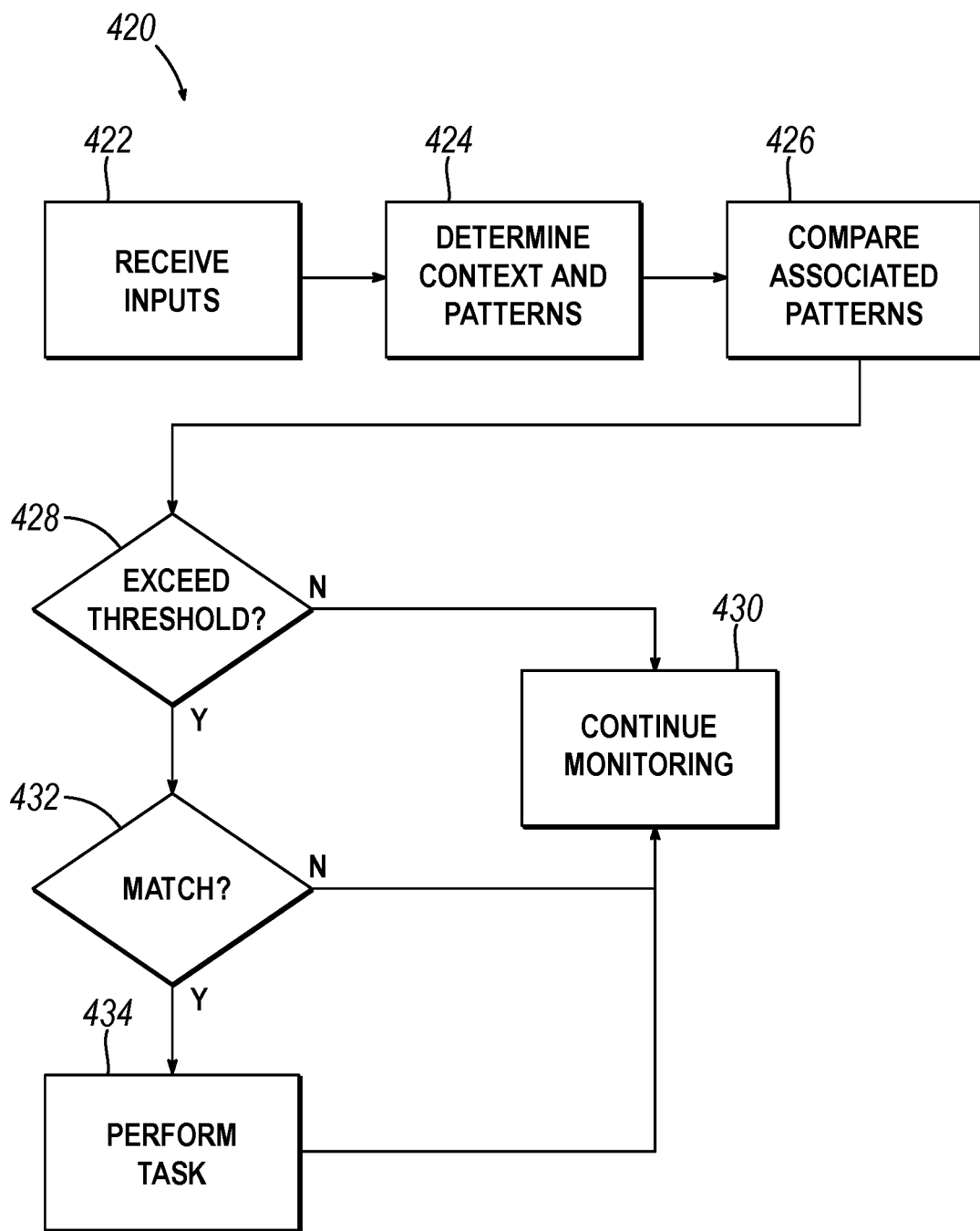
FIG. 7 depicts an exemplary set of steps that may be performed to identify movement patterns.

FIG. 7 shows an exemplary set of steps (420) that may be performed to monitor for and identify movement patterns within motion input received from a tracked device or instrument within the tracked field (300). When the IGS navigation system (10) is actively tracking instruments within the tracked field (300), the positions of one or more tracked instruments may be determined by the IGS navigation system (10) in near real-time as they move. When monitoring for control patterns, the IGS navigation system (10) may save portions of the same movement data for instruments as they are received (block 422) in order to analyze them for control patterns. As input is received (block 422), the context for the input may be determined (block 424), and any configured control patterns that are valid for that input context may be compared (block 426) to the input to determine if there are any matching control patterns.

For example, if input is received (block 422) from the registration probe (100) during registration of a patient's face, the system may determine (block 424) that the input is being received during registration, and may determine that there are no valid control patterns to evaluate. Where input is received (block 422) from the registration probe (100) in another context (e.g., post-registration, or based upon a button press or mode change), the system may determine (block 424) that context and identify a control pattern for the registration probe (100) moving along the x-axis (308) and y-axis (308). Those control patterns may then be compared (block 426) to or evaluated against the received input (block 422) for matches.

When comparing (block 426), if there are any thresholds associated with the control pattern (e.g., pattern specific or global), the system may determine whether the threshold is met (block 428) or whether any other filters apply. If the threshold is not met (block 428) for an evaluated pattern it will be disregarded, and if the input doesn't meet the threshold requirements for any associated patterns then the received (block 422) input is determined to be unrelated to any configured motion control pattern. This may occur where, for example, input is received (block 422) from a movement of the registration probe that indicates a very small or very slow motion, which may be unintentional, or where moderate movement is detected along the z-axis (312), but the system is configured to only detect large movements on that axis, as may be configured for a particular system.

Where any configured thresholds or filters are met (block 428), the system may apply a pattern recognition process to determine if the received input (block 422) appears to be a good match for the configured (block 414) spatial input. Where a particular pattern does not match (block 432) it may be disregarded, and where no pattern matches the received (block 422) input the system may continue monitoring (block 430) for subsequent inputs. Where the received (block 422) input does match a control pattern, the system may perform (block 432) any tasks configured for the detected control pattern. For example, this may include determining that movement of the registration probe (100) in two dimensions (e.g., relative to the first canvas (302)) matches (block 432) a corresponding control pattern to detect such movements, and performing (block 432) the associated task of moving a cursor on the display screen (16) a corresponding distance in a corresponding direction.

Figure 8:
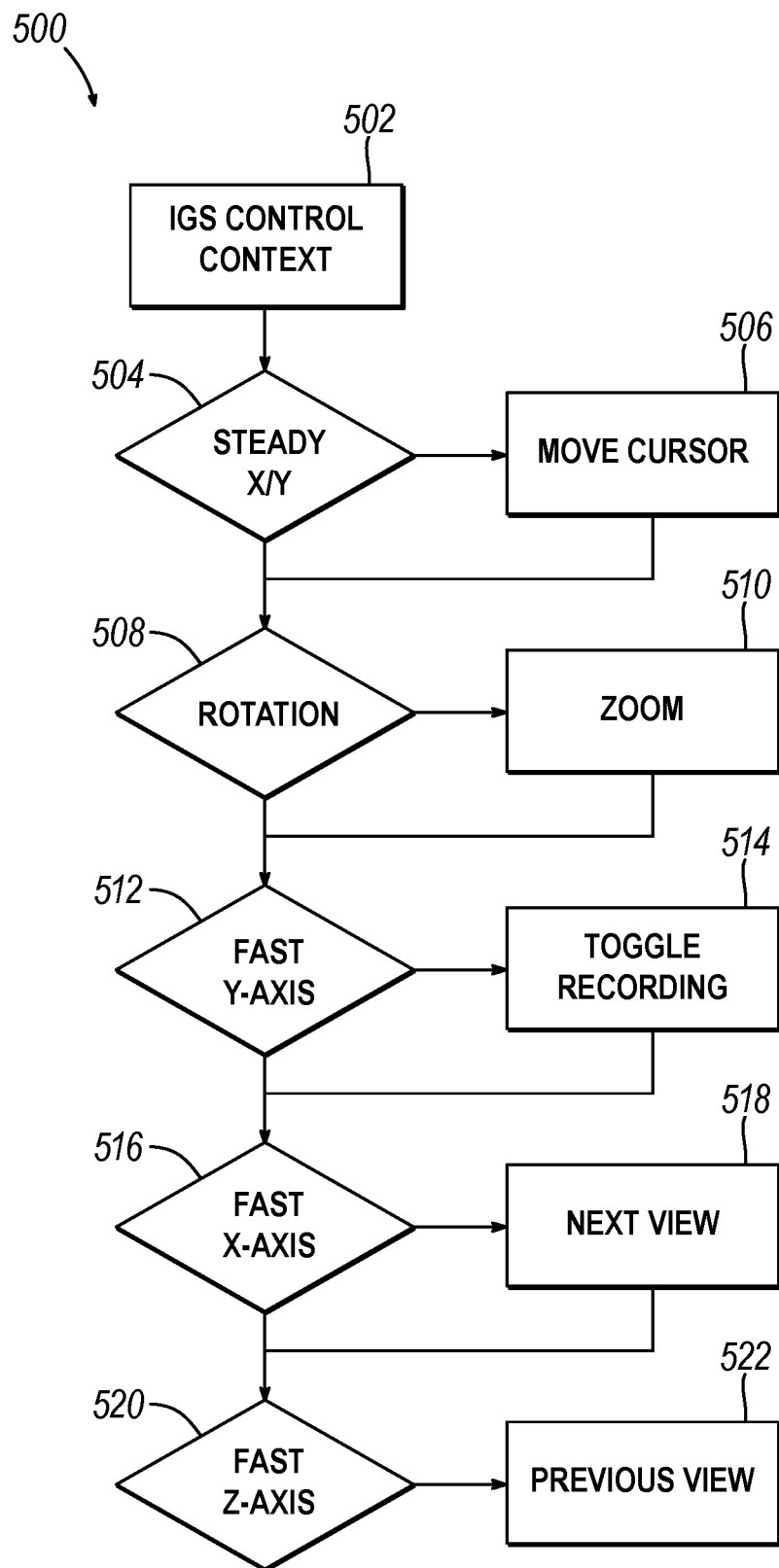
FIG. 8 depicts an exemplary set of steps that may be performed to act upon one or more pattern-based inputs.
Figure 9:
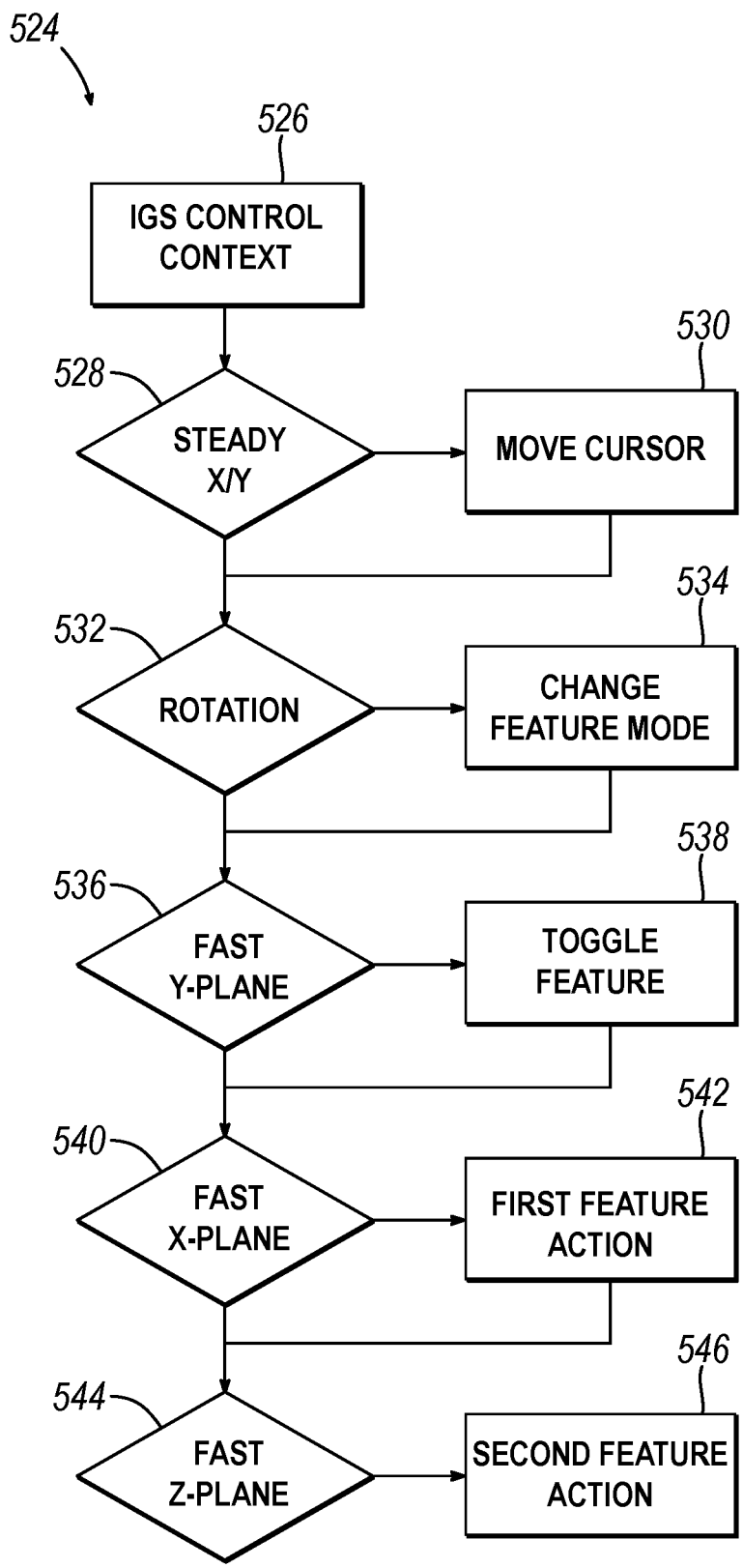
FIG. 9 depicts an exemplary set of steps that may be performed in an alternate implementation to act upon one or more pattern-based inputs.

While the descriptions above provide exemplary methods for configuring and using control patterns, FIGS. 8-9 provide examples of particular control pattern schemes that may be implemented for a system such as the IGS navigation system (10) while tracking the registration probe (100), the suction tool (200), or another tracked device. For example, FIG. 8 depicts an exemplary set of steps (500) that may be performed to act upon one or more pattern-based inputs. The steps of FIG. 8 represent one exemplary set of motion controls that may be configured, and assume that one or more steps such as those described in the context of FIGS. 5-7 have already been performed to monitor motion inputs and identify a configured control pattern. Where the matching input is a steady movement (block 504) along the x-axis (308), the y-axis (310), or both, the system may move (block 506) a cursor on the display screen (16) in a corresponding direction and distance.

Figure 10A:
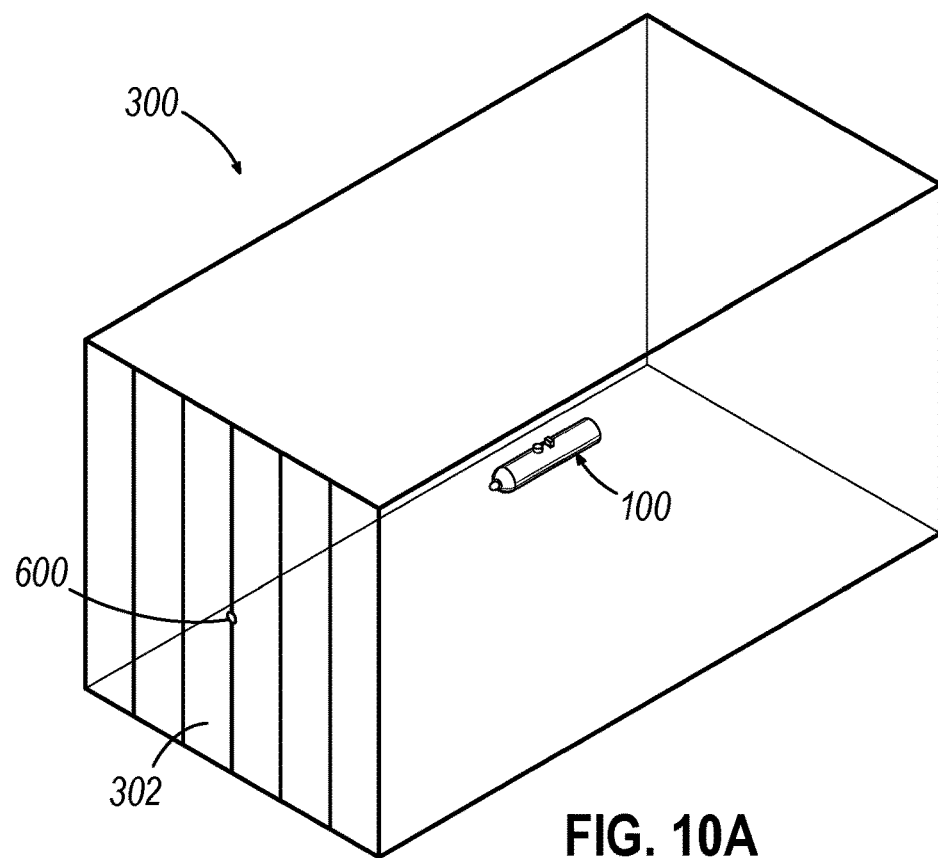
FIG. 10A depicts a diagram showing the position of the registration probe of FIG. 2 relative to a control canvas.
Figure 10B:
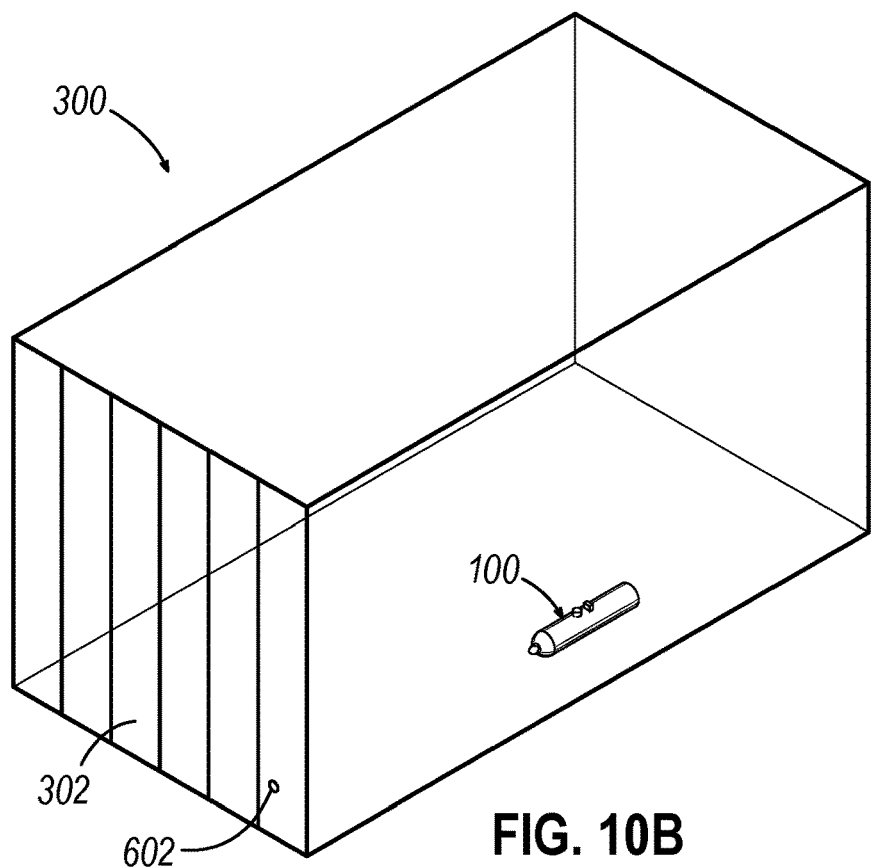
FIG. 10B depicts a diagram showing the position of the registration probe of FIG. 2 relative to the control canvas of FIG. 10A after a movement.
Figure 11A:
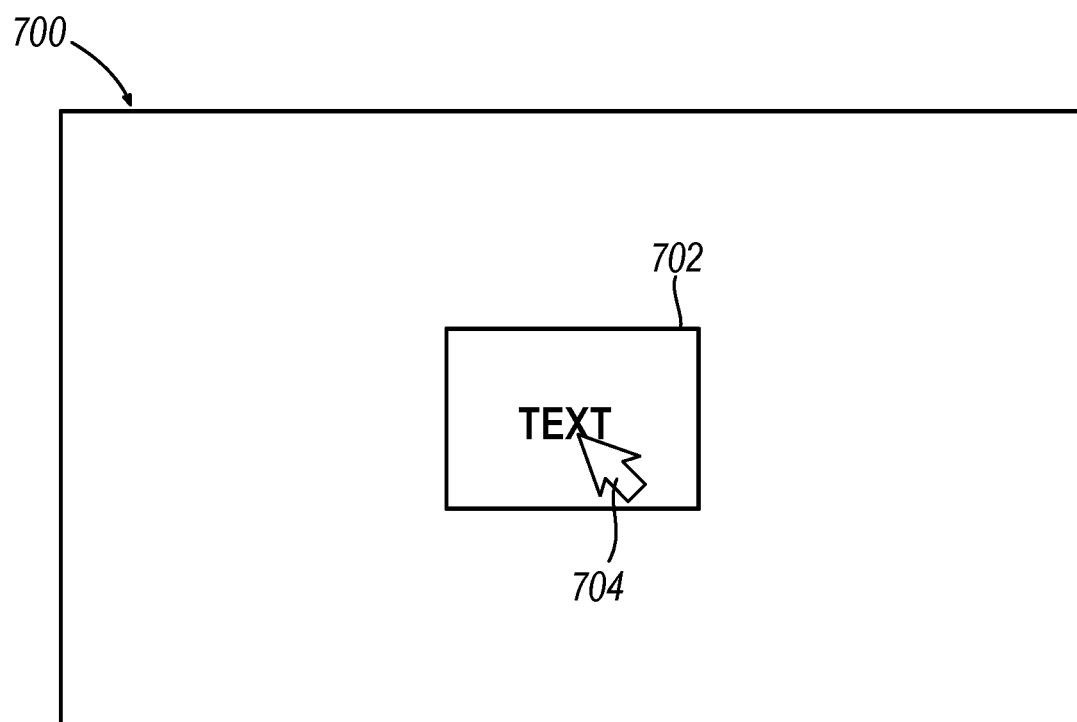
FIG. 11A depicts a screenshot of an exemplary image guided surgery (IGS) display associated with the arrangement shown in FIG. 10A.
Figure 11B:
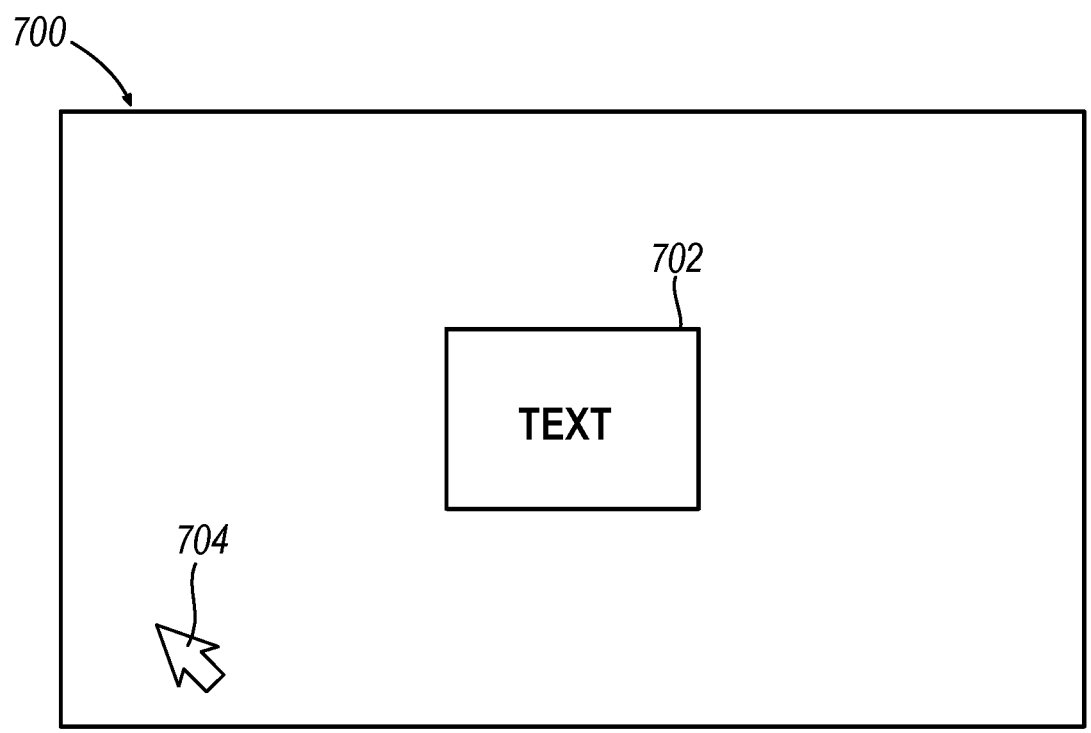
FIG. 11B depicts a screenshot of the IGS display associated with the arrangement shown in FIG. 10B.

FIGS. 10A and 10B each show the tracked space (300), with the registration probe's (100) position projected onto the first canvas (302) and corresponding to a cursor position on the display screen (16), as shown in FIGS. 11A and 11B. As a note, when described herein as being projected onto a canvas, it should be understood that this is a descriptive term intended to aid in visualizing the movement of the registration probe (100) within the tracked space (300), relative to a specified viewpoint (e.g., the first canvas (302)). As such, the IGS navigation system (10) is not required to create corresponding software objects for canvases or projected points, or perform corresponding actions, though in some implementations it may do so. In FIG. 10A, the registration probe (100) is positioned at the approximate midpoint of the first canvas (302), as can be seen by the position (600) projected onto the first canvas (302). In FIG. 11A, the position (600) corresponds to the position of a cursor (704) in an interface (700) that may be displayed on the display screen (16) or another device. An interface element (702) may be readable text, an image, a clickable button or other control, or another similar feature that a user may wish to interact with in an interface of the IGS navigation system (10).

In FIG. 10B, the registration probe (100) has been moved downwards and to the right within the tracked space (300), as can be seen by the position (602) projected onto the first canvas (302). In FIG. 11B, the position (602) corresponds to the position of the cursor (704), which has moved a direction and distance corresponding to the movement of the registration probe (100) within the tracked space (300). In this manner, it can be seen that the registration probe (100 can be used to control the movements of the cursor (704), and interact with objects such as the interface element (702), without requiring a contact surface such as an optical mouse or other device might require. Position tracking of the registration probe (100) may be used to position the cursor as described, while inputs via the first button (102) and the second button (104) may be received as clicks, activations or other interactions with targeted interface elements. For example, a user may move the registration probe (100) within the tracked area (300) until it rests above the interface element (702) which maybe a navigation control of the IGS navigation interface (e.g., used to move or rotate a virtual endoscopic view), and then click the first button (102) to activate the interface element (702). Where the tracked surgical instrument is the suction tool (200) or another surgical instrument lacking additional inputs such as the first button (102), a selection or activation may be configured as a detectable control pattern, such as a steady movement along the z-axis (312), or a swinging motion along the y-axis (310) and the z-axis (312) from the perspective of the second canvas (304).

Further since the registration probe (100), the suction tool (200), or another surgical instrument is already intended for use during a surgical procedure, it may provide such functionality without introducing an additional device or tool to the surgical area (e.g., as a stand-alone non-contact pointing device might) or requiring special implementation considerations (e.g., specially designing a mouse, keyboard, or other conventional input device to make it suitable for sterile procedure use and sterilization).

Figure 10C:
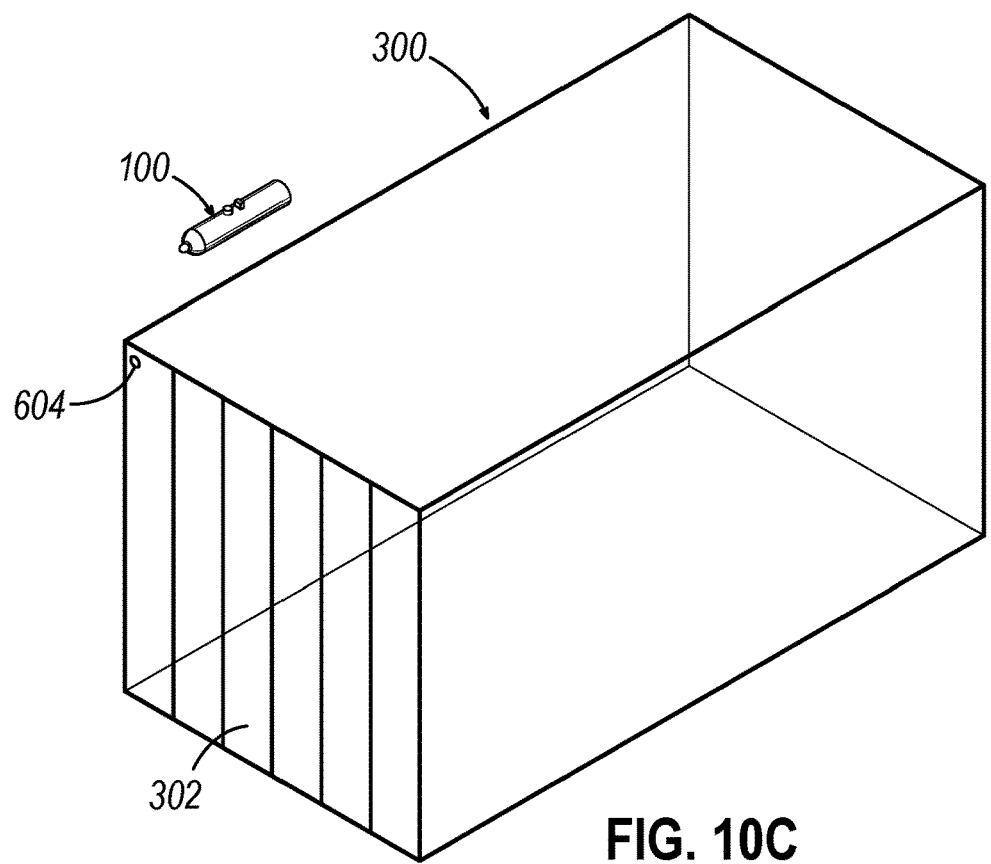
FIG. 10C depicts a diagram showing the position of the registration probe of FIG. 2 relative to the control canvas of FIG. 10A after being removed from the tracked space.
Figure 11C:
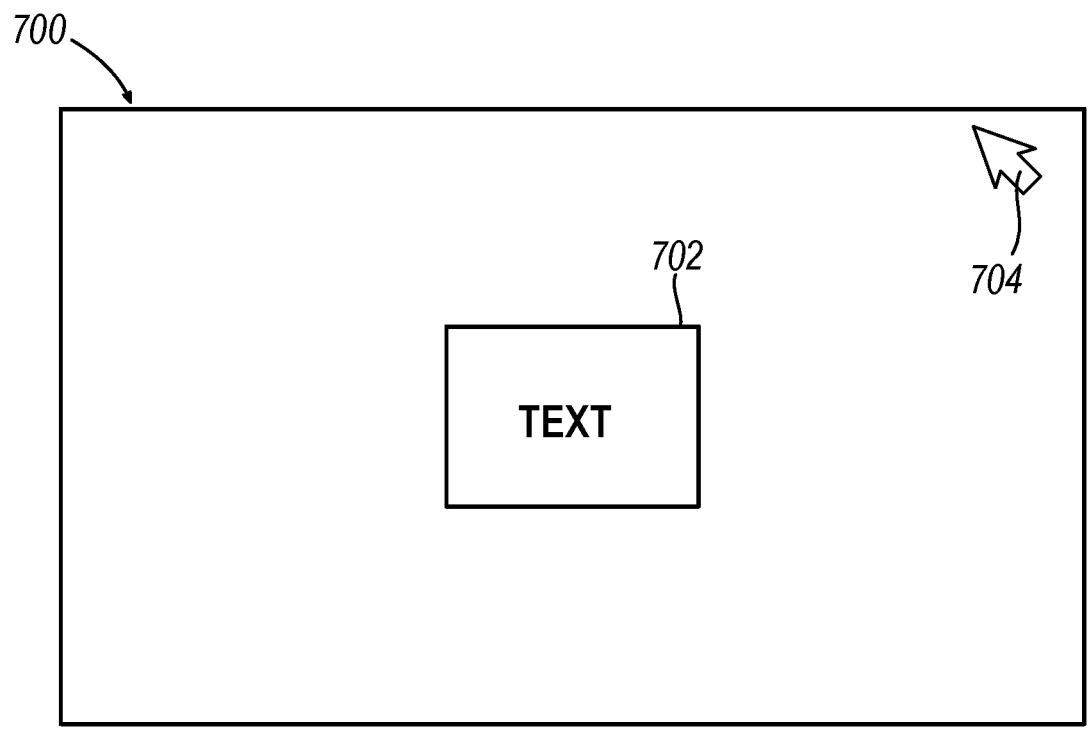
FIG. 11C depicts a screenshot of the IGS display associated with the arrangement shown in FIG. 10C.

FIGS. 10C and 11C show a similar scenario. In FIG. 10C, it can be seen that the registration probe (100) has been moved entirely outside of the tracked space (300), with the position (604) being projected onto the first canvas (302) at the last position that the registration probe (100) was detected at. In FIG. 11C, it can be seen that cursor (704) has been corresponding moved in the interface (700), and may stay there until the registration probe (100) is returned to the tracked space (300).

Figure 10D:
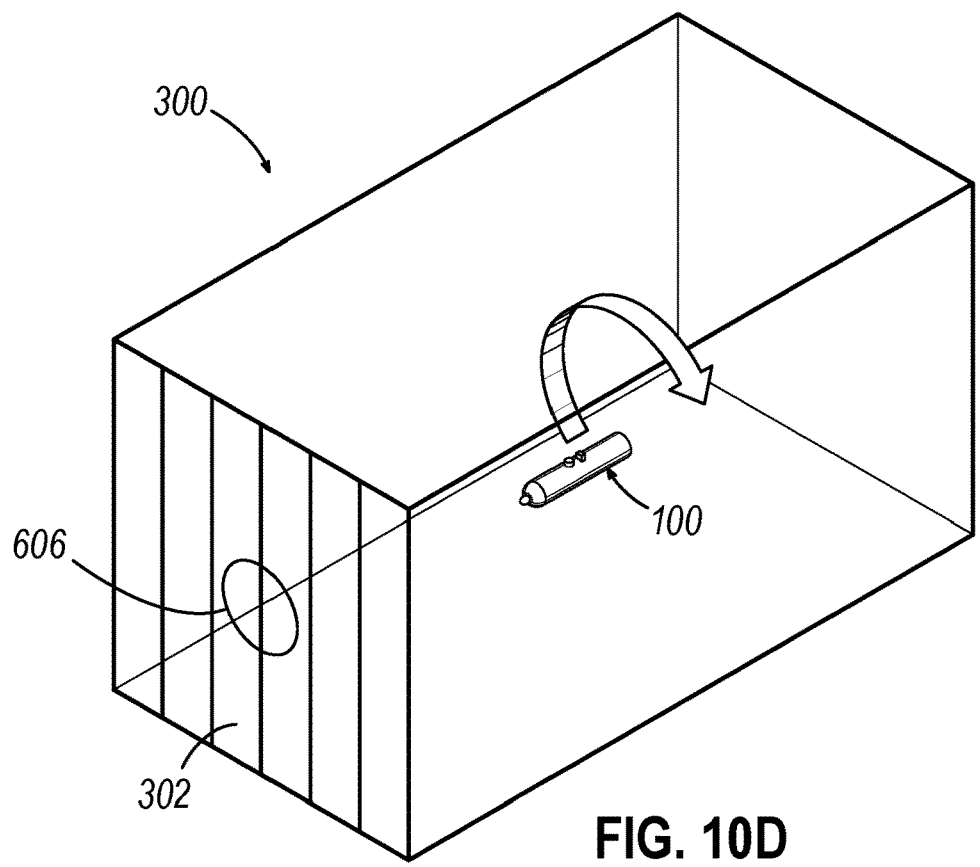
FIG. 10D depicts a diagram showing the position of the registration probe of FIG. 2 relative to the control canvas of FIG. 10A during a rotational movement.
Figure 11D:
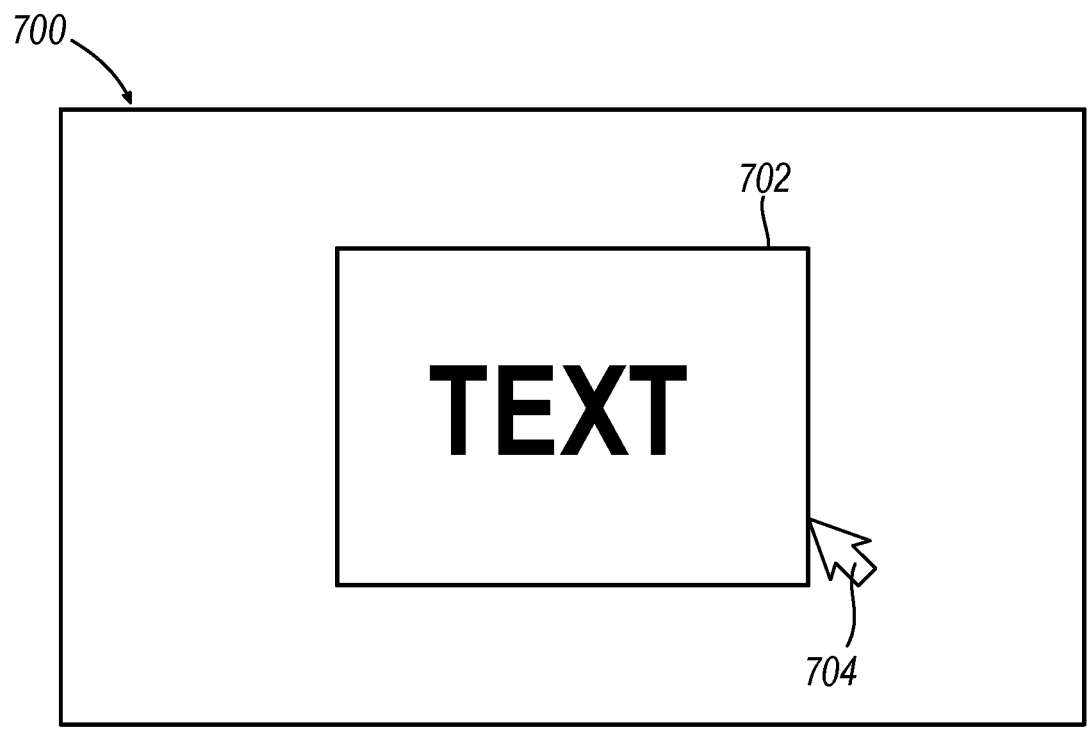
FIG. 11D depicts a screenshot of the IGS display associated with the arrangement shown in FIG. 10D.

Returning to FIG. 8, the IGS navigation system (10) may also be configured to identify motion patterns of various shapes, such as circular pattern or rotation (block 508). Where the matching input is a rotation (block 508), the system may zoom (block 510) an interface shown on the display screen (16) a corresponding amount, either increasing the magnification of the displayed interface (e.g., as a result of a clockwise rotation), or decreasing the magnification of the displayed interface (e.g., as a result of a counter-clockwise rotation). FIGS. 10D and 11D show an example of such a feature. In FIG. 10D, the registration probe (100) has been rotated, causing a circular pattern (606) to be projected onto the first canvas (302). FIG. 11D shows that the interface (700) has been zoomed in, causing the interface element (702) to be magnified, which may make text easier to read, may enlarge images to show more detail, or may otherwise make the interface easier to interact with. Repeated circular motions such as that shown in FIG. may cause the interface to continually zoom (block 510) to increase magnification, while circular motions in the reverse direction may cause the interface to zoom (block 510) to decrease magnification.

Returning again to FIG. 8, the IGS navigation system may also be configured to identify a fast movement (block 512)

primarily along the y-axis (310), a fast movement (block 516) primarily along the x-axis (308), or a fast movement (block 520) primarily along the z-axis (312). Fast movements may be differentiated from steady movements (block 504) based upon such factors as the acceleration, speed, and frequency of the movement. For example, where the registration probe (100) is moved such that its acceleration reaches a threshold, its maximum speed reaches a threshold, its motion is repetitive (e.g., moved back and forth), or is primarily along one axis (e.g., moved entirely or substantially along the x-axis (308) with little movement along the y-axis (310), it may be determined to be a fast movement as opposed to a steady movement.

When a fast movement is detected (block 512) along the y-axis (310), the IGS navigation system (10) may toggle (block 514) a recording mode to cause images or video to be captured from an endoscope, a virtual endoscopic view, or another display in use by the IGS navigation system (10). In this manner, a user of the registration probe (100) may rapidly move the device up and down in order to save images for later review and use, or activate other functions.

When a fast movement is detected (block 516) along the x-axis (308), the IGS navigation system (10) may advance a view displayed on the display screen (16) to a next view (block 518), while a fast movement detected (block 520) along the z-axis (312) may reverse the view displayed on the display screen (16) to a previous view (block 522). This may be useful to quickly change the position and orientation of a virtual camera, or virtual viewpoint, from which the virtual endoscopic view provided by the IGS navigation system (10) is being viewed. For example, a number of pre-set positions and orientations may be configured to view an anatomical structure or surgical site from different positions and orientations that will provide useful views for positioning and operating tracked surgical instruments. In such a case, a user may rapidly move the registration probe (100) along either axis in order to navigate between such views as desired. As another example, rapid movement along either axis may cause the IGS navigation system to move to a next view (block 518) or previous view (block 522) within a set of tomographic images (e.g., may cause the next or previous image in a layer of many tomographic images to be displayed, with each movement advancing one or more images through the set).

The set of control patterns of FIG. 8 are exemplary, and may be useful and intuitive in providing a wide functionality for a user of the registration probe (100), the suction tool (200), or another device. However, different control patterns exist. For example, FIG. 9 depicts an exemplary set of steps (524) that may be performed in an alternate implementation within an IGS control context (block 526) to act upon one or more pattern-based inputs, including steady movement (block 528) along one or more of the x-axis (308) and y-axis (310), rotational movement (block 532), fast movement (block 536) along the y-axis (310), fast movement (block 540) along the x-axis (308), and fast movement (block 544) along the z-axis (312), each as described above in the context of FIG. 8. In this implementation, steady movement (block 528) also results in movement (block 530) of the cursor, also as described in FIG. 8. Rotation (block 532) results in the IGS navigation system (10) changing (block 534) between feature modes, which may include, for example, an image capture feature, a zoom feature, an image navigation feature, and other feature sets, with a rotation in a first direction switching to a next feature, and a rotation in the second direction returning to a previous feature.

Fast movements along each individual axis may cause the IGS navigation system (10) to toggle (block 538) a feature specific action (e.g., start or stop recording, zoom in or zoom out, advance or reverse through image sets or viewpoints), activate a first feature specific action (block 542) (e.g., capture an image instead of a video, advance to a specific zoom point), or activate a second feature specific action (block 546) (e.g., capture a time lapse of images at set intervals, steadily change zoom levels until a subsequent input is received). When changing (block 534) between feature modes, the display screen (16) may display the current mode so that a user knows which feature sets and actions are available at any given time, since such features may be dependent upon the current feature mode. A control pattern configuration such as that shown in FIG. 9 may advantageously allow many different feature modes to be supported, each having their own features and actions, using a basic set of easily recreated motions (e.g., steady movements, rotations, fast movements). In this manner, a user may master a small set of control patterns, and access different feature modes as desired to support many different feature sets.

In view of the foregoing, it should be understood that a registration probe (100) may be used in two completely different ways during two separate stages of an IGS navigation system (10) guided medical procedure. In the pre-operative stage, registration probe (100) may be used to register anatomical landmarks on a patient's head (H) with the IGS navigation system (10), thereby enabling the IGS navigation system (10) to correlate preoperatively obtained images or digital models of the patient's head (H) with the actual location of the patient's head (H) in a tracked space (300). During the operative stage of the IGS navigation system (10) guided medical procedure, the same registration probe (100) may be used as a user input device to interact with the IGS navigation system (10) and control how information, images, etc. are rendered or otherwise manipulated on display screen (16). This may be much more convenient and efficient for the surgeon, as it allows the surgeon to avoid interacting with a keyboard or mouse. Moreover, the registration probe (100) may be placed on the patient's chest or some other location that is conveniently accessible to the surgeon.

As also noted above, in facilities where different surgeons use the same IGS navigation system (10), the IGS navigation system (10) may store each surgeon's unique registration probe (100) movements and associated commands in separate profiles associated with each surgeon. Thus, if a surgeon had previously established a set of registration probe (100) movements and associated commands, the IGS navigation system (10) may pull that surgeon's profile from the stored set of profiles without requiring the surgeon to re-train the IGS navigation system (10) on that surgeon's particular registration probe (100) movements and associated commands.

While registration probe (100) is used as a user input device to manipulate views provided via IGS navigation system (10) and to otherwise control certain aspects of operation of IGS navigation system (10) (e.g., starting and stopping the recordation of video, etc.) during an operative stage of a medical procedure, it should be understood that other instruments having one or more position sensors may also be used in a similar fashion. By way of example only, suction tool (200) or any other kind of sensor-equipped surgical instrument may be used just like registration probe (100) as a user input device to manipulate views provided via IGS navigation system (10) and to otherwise control certain aspects of operation of IGS navigation system (10) (e.g., starting and stopping the recordation of video, etc.) during an operative stage of a medical procedure.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An image guided surgery (IGS) navigation system comprising: an instrument including a position sensor; a tracking field generator operable to provide a tracked area, wherein the tracked area is a three dimensional space; a processor configured to determine a position of the instrument within the tracked area based upon a set of tracking data, wherein the set of tracking data is based on signals from the position sensor received by the processor as a result of an interaction of the instrument with the tracked area; a display operable by the processor to provide an IGS navigation interface to a user; and a memory configured to store a set of control patterns, wherein each of the set of control patterns comprises a spatial input; wherein the processor is further configured to: determine a motion of the instrument within the tracked area based on a plurality of positions determined for the instrument, determine if any control pattern of the set of control patterns is associated with the motion based upon a comparison of the spatial input for that control pattern with the motion, and where a control pattern of the set of controls patterns is associated with the motion, determine an interface action associated with the control pattern and execute the interface action on the IGS navigation interface.

Example 2

The IGS navigation system of Example 1, wherein the tracking field generator comprises a set of magnetic field generators operable to produce a magnetic field at the tracked area, and wherein the position sensor is configured to generate position-indicative signals in response to presence of the position sensor in the magnetic field.

Example 3

The IGS navigation system of any one or more of Examples 1 through 2, wherein the instrument comprises a registration probe.

Example 4

The IGS navigation system of any one or more of Examples 1 through 3, wherein the control pattern comprises a speed threshold, the spatial layout for the control pattern describes motion in two dimensions at a speed less than the speed threshold, and the interface action associated with the control pattern describes movement of a cursor on the IGS navigation interface, wherein the processor is further configured to: determine a direction of the motion in two dimensions, determine a distance of the motion, and move the cursor on the IGS navigation interface based on the direction and the distance.

Example 5

The IGS navigation system of Example 4, wherein a second control pattern of the set of control patterns comprises a second speed threshold, wherein the spatial layout for that control pattern describes motion in one dimension at a speed greater than the second speed threshold, wherein the second speed threshold is greater than or equal to the speed threshold, and wherein a second interface action is associated with the second control pattern.

Example 6

The IGS navigation system of Example 5, wherein the processor is further configured to: where the second interface action describes an image capture mode of the IGS navigation interface, capture one or more images of a virtual endoscopic view currently displayed on the IGS navigation interface, and where the second interface action describes a view change of the IGS navigation interface, change the virtual endoscopic view from a first view to a second view.

Example 7

The IGS navigation system of any one or more of Examples 1 through 6, wherein the spatial layout for the control pattern describes a rotational motion, and the interface action associated with the control pattern is magnification of the IGS navigation interface, wherein the processor is further configured to: determine a magnification level based on the rotational motion, and magnify the display of the IGS navigation interface based on the magnification level.

Example 8

The IGS navigation system of Example 7, wherein the processor is further configured to: determine a direction of the rotational motion, increase the magnification of the IGS navigation interface when the direction is a first direction, and decrease the magnification of the IGS navigation interface when the direction is a second direction oppose of the first direction.

Example 9

The IGS navigation system of any one or more of Examples 1 through 8, wherein each of the set of control patterns is associated with an input context, and wherein the processor is further configured to: determine a current input context associated with the motion, and when determining if any control pattern of the set of control patterns is associated with the motion, only compare control patterns within the set of control patterns whose input context matches the current input context.

Example 10

The IGS navigation system of Example 9, wherein the processor is further configured to determine the current input context based upon: a type of the instrument, and a current stage of a surgical procedure being performed with the IGS navigation system.

Example 11

The IGS navigation system of any one or more of Examples 9 through 10, the instrument further comprising a mode control operable to place the instrument in a motion control mode, wherein the processor is further configured to determine the current input context based upon whether the instrument is in the motion control mode.

Example 12

The IGS navigation system of any one or more of Examples 1 through 11, wherein the processor is further configured to: determine the interface action associated with the control pattern based upon a current feature mode, selected from a set of feature modes, that is configured for the instrument, when the motion is associated with a first control pattern, change the current feature mode to a different feature mode of the set of feature modes, and when the motion is associated with a second control pattern, activate a feature of the IGS navigation interface based upon the current feature mode.

Example 13

The IGS navigation system of any one or more of Examples 1 through 12, wherein the set of feature modes comprises: an image capture feature mode usable to capture images displayed on the IGS navigation interface, a view navigation mode usable to navigate between pre-set virtual endoscopic views displayed on the IGS navigation interface, and a zoom mode usable to change a magnification level of the IGS navigation interface.

Example 14

The IGS navigation system of any one or more of Examples 1 through 13, wherein the processor is further configured to: determine the motion of the instrument based upon a change in position in a first dimension and a second dimension, and when determining the motion of the instrument, disregard a change in position in a third dimension unless the change in position in the third dimension exceeds a configured distance threshold.

Example 15

A method comprising: operating an image guided surgery (IGS) navigation system to provide a tracked area, wherein the tracked area is a three-dimensional space, at a processor of the IGS navigation system, determining a set of positions of an instrument within the tracked area based on a set of tracking data received by a processor as a result of an interaction of the instrument with the tracked area, providing an IGS navigation interface to a user via a display of the IGS navigation system, storing a set of control patterns on a memory of the IGS navigation system, wherein each of the set of control patterns comprises a spatial input, determining a motion of the instrument within the tracked area based on a plurality of positions determined for the instrument based on signals from a position sensor in the instrument, determining if any control pattern of the set of controls patterns is associated with the motion based upon a comparison of the spatial input for that control pattern with the motion, and where a control pattern of the set of controls patterns is associated with the motion, determining an interface action associated with the control pattern and executing the interface action on the IGS navigation interface.

Example 16

The method of Example 15, wherein the control pattern comprises a speed threshold, the spatial layout for the control pattern describes motion in two dimensions at a speed less than the speed threshold, and the interface action associated with the control pattern describes movement of a cursor on the IGS navigation interface, the method further comprising: determining a direction of the motion in two dimensions; determining a distance of the motion; and moving the cursor on the IGS navigation interface based on the direction and the distance.

Example 17

The method of Example 16, wherein a second control pattern of the set of control patterns comprises a second speed threshold, wherein the spatial layout for that control pattern describes motion in one dimension at a speed greater than the second speed threshold, wherein the second speed threshold is greater than or equal to the speed threshold, and wherein a second interface action is associated with the second control pattern.

Example 18

The method of any one or more of Examples 15 through 17, wherein the spatial layout for the control pattern describes a rotational motion, and the interface action associated with the control pattern is magnification of the IGS navigation interface, the method further comprising: determining a magnification level based on the rotational motion; and magnifying the display of the IGS navigation interface based on the magnification level.

Example 19

The method of any one or more of Examples 15 through 18, further comprising: determining the motion of the instrument based upon a change in position in a first dimension and a second dimension; and when determining the motion of the instrument, disregarding a change in position in a third dimension unless the change in position in the third dimension exceeds a configured distance threshold.

Example 20

A system comprising: an instrument including a position sensor; a tracking field generator operable to provide a tracked area, wherein the tracked area is a three dimensional space; a processor configured to determine a position of the instrument within the tracked area based upon a set of tracking data obtained via a signal from the position sensor, wherein the set of tracking data is received by the processor as a result of an interaction of the instrument with the tracked area; and a display operable by the processor to provide an IGS navigation interface to a user; wherein the processor is further configured to: determine a training motion of the instrument within the tracked area based on a first plurality of positions determined for the instrument, receive an interface action from a user, and create a control pattern based on the training motion and the interface action, during a surgical procedure, determine a motion of the instrument within the tracked area based on a second plurality of positions determined for the instrument, compare the motion to the control pattern and determine if the motion is associated with the training motion, and where the control pattern is associated with the motion, execute the interface action on the IGS navigation interface.

V. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one skilled in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An image guided surgery (IGS) navigation system comprising:
   (a) an instrument including a position sensor;
   (b) a tracking field generator operable to provide a tracked area, the tracked area being a three dimensional space;
   (c) a display operable to provide an IGS navigation interface to a user;
   (d) a memory storing a set of control patterns, each of the set of control patterns comprising a spatial input, each of the set of control patterns corresponding to a gesture-based interface action; and
   (e) a processor configured to:
      (i) receive signals from the position sensor as a result of an interaction of the instrument with the tracked area,
      (ii) determine a motion of the instrument based upon a change in position of the instrument in a first dimension and a second dimension,
      (iii) when determining the motion of the instrument, disregard a change in position in a third dimension unless the change in position in the third dimension exceeds a configured distance threshold, and
      (iv) where at least one control pattern of the set of control patterns matches the motion based upon a comparison of the spatial input for the at least one control pattern with the motion, determine the gesture-based interface action corresponding to the at least one control pattern and execute the gesture-based interface action on the IGS navigation interface.

2. The IGS navigation system of claim 1, the tracking field generator comprising a set of magnetic field generators operable to produce a magnetic field at the tracked area, and the position sensor being configured to generate position-indicative signals in response to presence of the position sensor in the magnetic field.

3. The IGS navigation system of claim 1, wherein the instrument comprises a registration probe.

4. The IGS navigation system of claim 1, a first control pattern of the set of control patterns comprising a speed threshold, the spatial layout for the first control pattern describing motion in two dimensions at a speed less than the speed threshold, and the interface action associated with the first control pattern describing movement of a cursor on the IGS navigation interface, the processor being further configured to:
(i) determine a direction of the motion in two dimensions,
(ii) determine a distance of the motion, and
(iii) move the cursor on the IGS navigation interface based on the direction and the distance.

5. The IGS navigation system of claim 4, a second control pattern of the set of control patterns comprising a second speed threshold, the spatial layout for the second control pattern describing motion in one dimension at a speed greater than the second speed threshold, the second speed threshold being greater than or equal to the speed threshold, and a second interface action being associated with the second control pattern.

6. The IGS navigation system of claim 5, the processor being further configured to:
(i) where the second interface action describes an image capture mode of the IGS navigation interface, capture one or more images of a virtual endoscopic view currently displayed on the IGS navigation interface, and
(ii) where the second interface action describes a view change of the IGS navigation interface, change the virtual endoscopic view from a first view to a second view.

7. The IGS navigation system of claim 1, the spatial layout for the at least one control pattern describing a rotational motion, and the interface action associated with the at least one control pattern being magnification of the IGS navigation interface, the processor being further configured to:
(i) determine a magnification level based on the rotational motion, and
(ii) magnify the display of the IGS navigation interface based on the magnification level.

8. The IGS navigation system of claim 7, the processor being further configured to:
(i) determine a direction of the rotational motion,
(ii) increase the magnification of the IGS navigation interface when the direction is a first direction, and
(iii) decrease the magnification of the IGS navigation interface when the direction is a second direction oppose of the first direction.

9. The IGS navigation system of claim 1, each of the set of control patterns being associated with an input context, and the processor being further configured to:
(i) determine a current input context associated with the motion, and
(ii) when determining if at least one control pattern of the set of control patterns is associated with the motion, only compare control patterns within the set of control patterns whose input context matches the current input context.

10. The IGS navigation system of claim 9, the processor being further configured to determine the current input context based upon:
(i) a type of the instrument, and
(ii) a current stage of a surgical procedure being performed with the IGS navigation system.

11. The IGS navigation system of claim 9, the instrument further comprising a mode control operable to place the instrument in a motion control mode, the processor being further configured to determine the current input context based upon whether the instrument is in the motion control mode.

12. The IGS navigation system of claim 1, the processor being further configured to:
(i) determine the interface action associated with the at least one control pattern based upon a current feature mode, selected from a set of feature modes, that is configured for the instrument,
(ii) when the motion is associated with a first control pattern, change the current feature mode to a different feature mode of the set of feature modes, and
(iii) when the motion is associated with a second control pattern, activate a feature of the IGS navigation interface based upon the current feature mode.

13. The IGS navigation system of claim 12, the set of feature modes comprising:
(i) an image capture feature mode usable to capture images displayed on the IGS navigation interface,
(ii) a view navigation mode usable to navigate between pre-set virtual endoscopic views displayed on the IGS navigation interface, and
(iii) a zoom mode usable to change a magnification level of the IGS navigation interface.

14. The IGS navigation system of claim 1, the processor being further configured to:
(i) receive the configured distance threshold from the user,
(ii) apply the configured distance threshold to all changes in position in the third dimension, and
(iii) determine a motion of the instrument based on a change in position in the third dimension if the change in position in the third dimension exceeds the configured distance threshold.

15. A method comprising:
(a) operating an image guided surgery (IGS) navigation system to provide a tracked area, the tracked area being a three-dimensional space;
(b) determining a set of positions of an instrument within the tracked area based on a set of tracking data received by a processor as a result of an interaction of the instrument with the tracked area;
(c) providing an IGS navigation interface to a user via a display of the IGS navigation system;
(d) storing a set of control patterns on a memory of the IGS navigation system, each of the set of control patterns comprising a spatial input, each of the set of control patterns corresponding to a gesture-based interface action;
(e) monitoring a motion of the instrument within the tracked area based on a plurality of positions determined for the instrument based on signals from a position sensor in the instrument;
(f) determining if at least one control pattern of the set of control patterns matches the motion based upon a comparison of a spatial input for the at least one control pattern with the motion; and
(g) where the at least one control pattern of the set of control patterns matches the motion, determining the gesture-based interface action corresponding to the at least one control pattern and executing the gesture-based interface action on the IGS navigation interface, the at least one control pattern comprising a speed threshold representing a threshold speed of the instrument, the spatial layout for the control pattern describing motion in two dimensions at a speed less than the speed threshold, and the interface action associated with the at least one control pattern describing movement of a cursor on the IGS navigation interface.

16. The method of claim 15, further comprising:
(a) determining a direction of the motion in two dimensions;
(b) determining a distance of the motion; and
(c) moving the cursor on the IGS navigation interface based on the direction and the distance.

17. The method of claim 16, a second control pattern of the set of control patterns comprising a second speed threshold, the spatial layout for that control pattern describing motion in one dimension at a speed greater than the second speed threshold, the second speed threshold being greater than or equal to the speed threshold, and a second interface action being associated with the second control pattern.

18. The method of claim 15, the spatial layout for the control pattern describing a rotational motion, and the interface action associated with the control pattern being magnification of the IGS navigation interface, the method further comprising:
(a) determining a magnification level based on the rotational motion; and
(b) magnifying the display of the IGS navigation interface based on the magnification level.

19. The method of claim 15, further comprising:
(a) determining the motion of the instrument based upon a change in position in a first dimension and a second dimension; and
(b) when determining the motion of the instrument, disregarding a change in position in a third dimension unless the change in position in the third dimension exceeds a configured distance threshold.

20. A method comprising:
(a) operating an image guided surgery (IGS) navigation system to provide a tracked area, the tracked area being a three-dimensional space;
(b) determining a set of positions of an instrument within the tracked area based on a set of tracking data received by a processor as a result of an interaction of the instrument with the tracked area;
(c) providing an IGS navigation interface to a user via a display of the IGS navigation system;
(d) storing a set of control patterns on a memory of the IGS navigation system, each of the set of control patterns comprising a spatial input, each of the set of control patterns corresponding to a gesture-based interface action;
(e) determining a motion of the instrument based upon a change in position in a first dimension and a second dimension;
(f) when determining the motion of the instrument, disregarding a change in position in a third dimension unless the change in position in the third dimension exceeds a configured distance threshold;
(g) determining if at least one control pattern of the set of control patterns matches the motion based upon a comparison of a spatial input for the at least one control pattern with the motion; and
(h) where the at least one control pattern of the set of control patterns matches the motion, determining the gesture-based interface action corresponding to the at least one control pattern and executing the gesture-based interface action on the IGS navigation interface.

* * * * *